(12) United States Patent
Cardosi et al.

(10) Patent No.: US 8,025,788 B2
(45) Date of Patent: Sep. 27, 2011

(54) METHOD FOR MANUFACTURING AN ENZYMATIC REAGENT INK

(75) Inventors: Marco F. Cardosi, Croy (GB); Michael O'Connell, Muir of Ord (GB)

(73) Assignee: LifeScan Scotland Limited (GB)

( * ) Notice: Subject to any disclaimer, the term of this patent is extended or adjusted under 35 U.S.C. 154(b) by 102 days.

(21) Appl. No.: 12/429,376

(22) Filed: Apr. 24, 2009

(65) Prior Publication Data

US 2010/0270151 A1  Oct. 28, 2010

(51) Int. Cl.
*G01N 33/48* (2006.01)
*C12Q 1/26* (2006.01)

(52) U.S. Cl. .................. 205/777.5; 422/82.01; 435/14; 436/72

(58) Field of Classification Search .......... 204/403.01, 204/403.14, 291; 205/777.5; 422/82.01; 435/14, 25; 436/72
See application file for complete search history.

(56) References Cited

U.S. PATENT DOCUMENTS

| | | | |
|---|---|---|---|
| 5,120,420 A | 6/1992 | Nankai et al. | |
| 5,288,636 A | 2/1994 | Pollmann et al. | |
| 5,628,890 A | 5/1997 | Carter et al. | |
| 5,708,247 A | 1/1998 | McAleer et al. | |
| 6,461,496 B1 | 10/2002 | Feldman et al. | |
| 6,863,800 B2 | 3/2005 | Karinka et al. | |
| 7,112,265 B1 | 9/2006 | McAleer et al. | |
| 7,250,105 B1 | 7/2007 | Davies et al. | |
| 7,291,256 B2 | 11/2007 | Teodorczyk et al. | |
| 7,462,265 B2 | 12/2008 | Leach et al. | |
| 7,465,380 B2 | 12/2008 | Rodgers et al. | |
| 2004/0026243 A1 | 2/2004 | Davies et al. | |
| 2006/0201805 A1 | 9/2006 | Forrow et al. | |
| 2006/0226006 A1 | 10/2006 | Rodgers et al. | |
| 2006/0226008 A1 | 10/2006 | Rodgers et al. | |
| 2006/0260940 A1 | 11/2006 | McAleer et al. | |

FOREIGN PATENT DOCUMENTS

| | | |
|---|---|---|
| EP | 0267724 B1 | 3/1992 |
| WO | WO 2004/039600 A2 | 5/2004 |
| WO | WO 2004/113917 A2 | 12/2004 |
| WO | WO 2006/096619 A2 | 9/2006 |

OTHER PUBLICATIONS

Webpage by Cabot Corporation, "CAB-O-SIL TS-610", Sep. 2008, 2 pgs.*
Material Safety Data Sheet by Dow Corning, "Dow Corning 544 Antifoam Compound", Dec. 2008, 8 pgs.*

(Continued)

*Primary Examiner* — Jeffrey T Barton
*Assistant Examiner* — J. Christopher Ball

(57) ABSTRACT

A method for manufacturing an enzymatic reagent ink for use in analytical test strips (such as electrochemical-based analytical test strips configured for the determination of glucose in blood) includes determining a first relationship between wetability of a representative hydrophobic silica material (e.g., a hydrophobic fumed silica material) and at least a first calibration characteristic (for example, a calibration slope) of an analytical test strip that includes an enzymatic reagent ink containing the representative hydrophobic silica material. In the method, the first relationship defines a minimum wetability that provides an acceptable first calibration characteristic. The method also includes determining a second relationship defining wetability of a mixture of a particular hydrophobic silica material and a particular surfactant across a range of relative amount of the particular hydrophobic silica material and the particular surfactant and, subsequently, combining an amount of the particular hydrophobic silica material, an amount of the particular surfactant, and an amount of enzyme (such as glucose oxidase) to form an enzymatic reagent ink. Moreover, the amounts of the particular hydrophobic silica material and the particular surfactant are predetermined based on the second relationship to provide at least the minimum wetability defined by the first relationship.

12 Claims, 4 Drawing Sheets

OTHER PUBLICATIONS

Naidu, BVK, et al. "Thermal, viscoelastic, solution, and membrane properties of sodium alginate/hydroxyethylcellulose blends", Carbohydrate Polymers, vol. 61, 2005, p. 52-60.*

European extended Search Report dated Jul. 23, 2010, corresponding to Application No. 10250820.7.

European extended Search Report dated Jul. 26, 2010, corresponding to Application No. 10250818.1.

European extended Search Report dated Jul. 26, 2010, corresponding to Application No. 10250819.9.

* cited by examiner

METHOD FOR MANUFACTURING AN ENZYMATIC REAGENT INK

BACKGROUND OF THE INVENTION

This application is related to the following co-pending applications: U.S. patent application Ser. No. 12/429,393, filing date Apr. 24, 2009 (now abandoned) and U.S. patent application Ser. No. 12/429,405, filing date Apr. 24, 2009 (now abandoned).

1. Field of the Invention

The present invention relates, in general, to reagent inks and, in particular, to enzymatic reagent inks, related manufacturing methods and related analytical test strips.

2. Description of Related Art

The use of enzymatic reagent inks in analytical test strips has experienced widespread commercial exploitation. For example, enzymatic reagent inks have been employed in electrochemical-based analytical test strips for the determination of glucose in whole blood samples. Such enzymatic reagent inks and analytical test strips are described in, for example, U.S. Pat. Nos. 7,465,380; 7,462,265; 7,291,256; 7,112,265; 5,708,247; 7,250,105; U.S. Pre-Grant Publication No. 2004/0026243; and International Publication No. WO2004039600, each of which is hereby incorporated in full by reference. The commercial exploitation of enzymatic reagent inks has consequentially led to an increased interest in the methods used to manufacture such inks.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings, of which:

DETAILED DESCRIPTION OF ILLUSTRATIVE EMBODIMENTS

The following detailed description should be read with reference to the drawings. The drawings depict exemplary embodiments for the purpose of explanation only and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Figure 1:
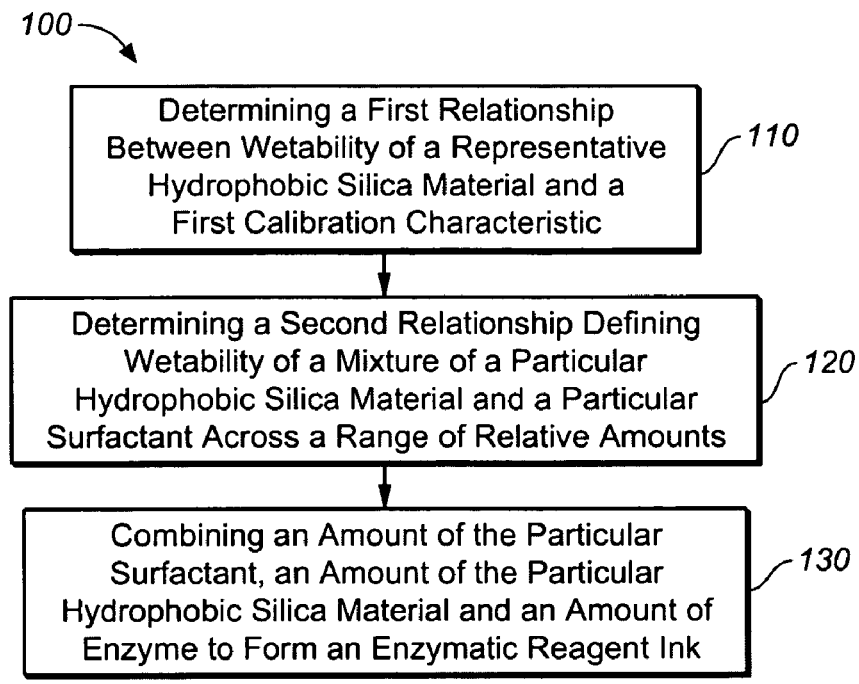
FIG. 1 is a flow diagram depicting stages in a process for manufacturing an enzymatic reagent ink according to an embodiment of the present invention.

FIG. 1 is a flow diagram depicting stages in a process 100 for manufacturing an enzymatic reagent ink (such as a screen printable enzymatic reagent ink with a viscosity in the range of 36,000 to 48,000 cP) for use in analytical test strips according to an embodiment of the present invention. Enzymatic reagent inks manufactured according to method 100 can be used in, for example, electrochemical-based analytical test strips configured for the determination of glucose in whole blood samples. Such electrochemical-based analytical test strips are described, with respect to conventional reagent inks, in, for example, U.S. Pat. Nos. 5,120,420; 5,288,636; 5,628,890; and 6,461,496.

Figure 6:
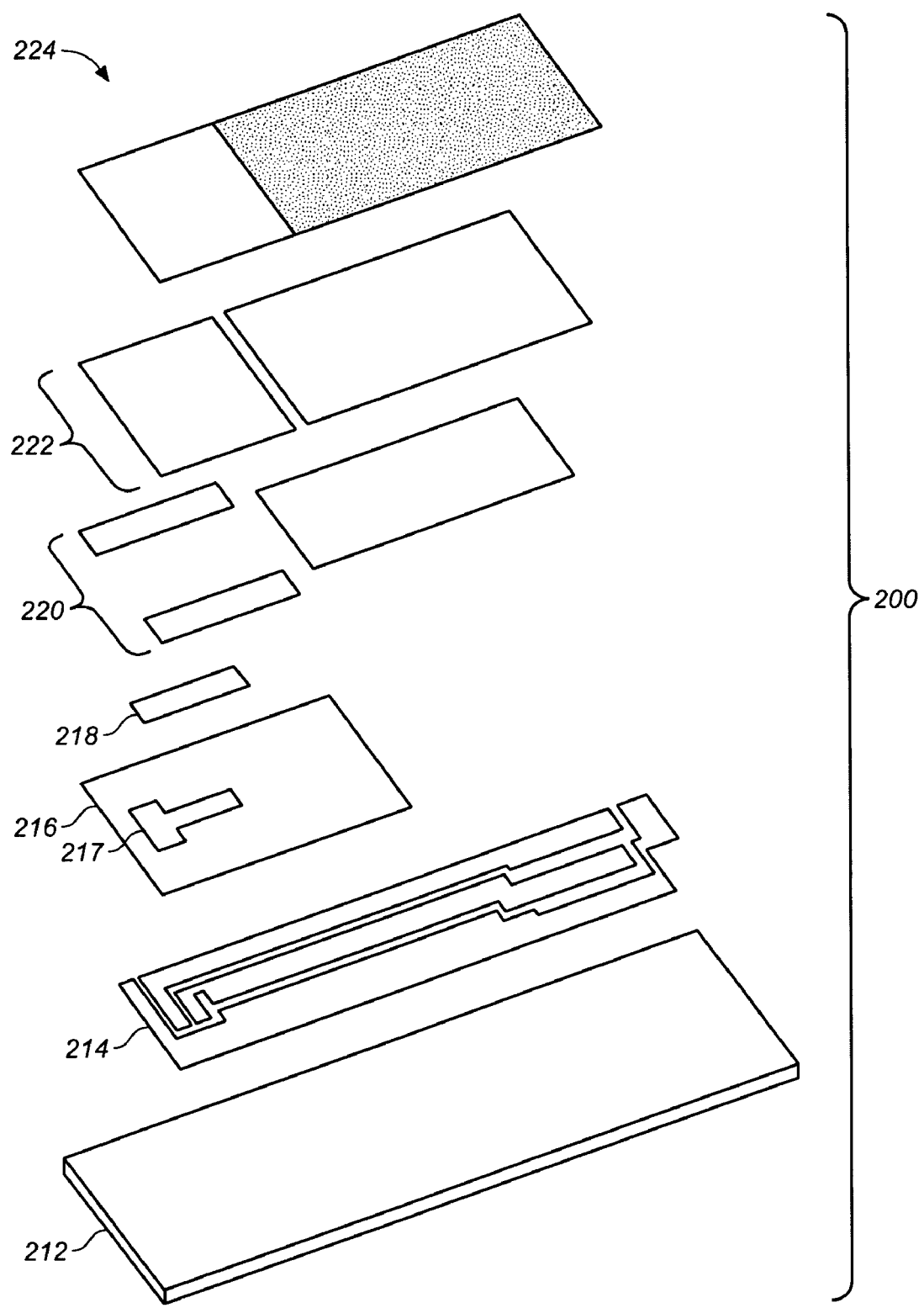
FIG. 6 is a simplified exploded perspective view of an analytical test strip according to an embodiment of the present invention.

In addition, an analytical test strip according to an embodiment of the present invention that employs an enzymatic reagent ink according to the present invention is depicted in FIG. 6 and described in the related discussion below. However, once apprised of the present disclosure, one of ordinary skill in the art can employ methods according to embodiments of the present invention to manufacture enzymatic reagent inks for any suitable type of analytical test strip.

Process 100 includes determining a first relationship between wetability of a representative hydrophobic silica material (e.g., a hydrophobic fumed silica material) and at least a first calibration characteristic (for example, a calibration slope and/or a calibration intercept) of an analytical test strip that includes an enzymatic reagent ink containing the representative hydrophobic silica material (see step 110 of FIG. 1). Moreover, the first relationship thus determined defines a minimum wetability that provides an acceptable first calibration characteristic. One skilled in the art will recognize that an "acceptable" calibration characteristic refers to characteristics that provide for suitably accurate and precise determination of an analyte of interest (e.g., glucose).

Figure 2:
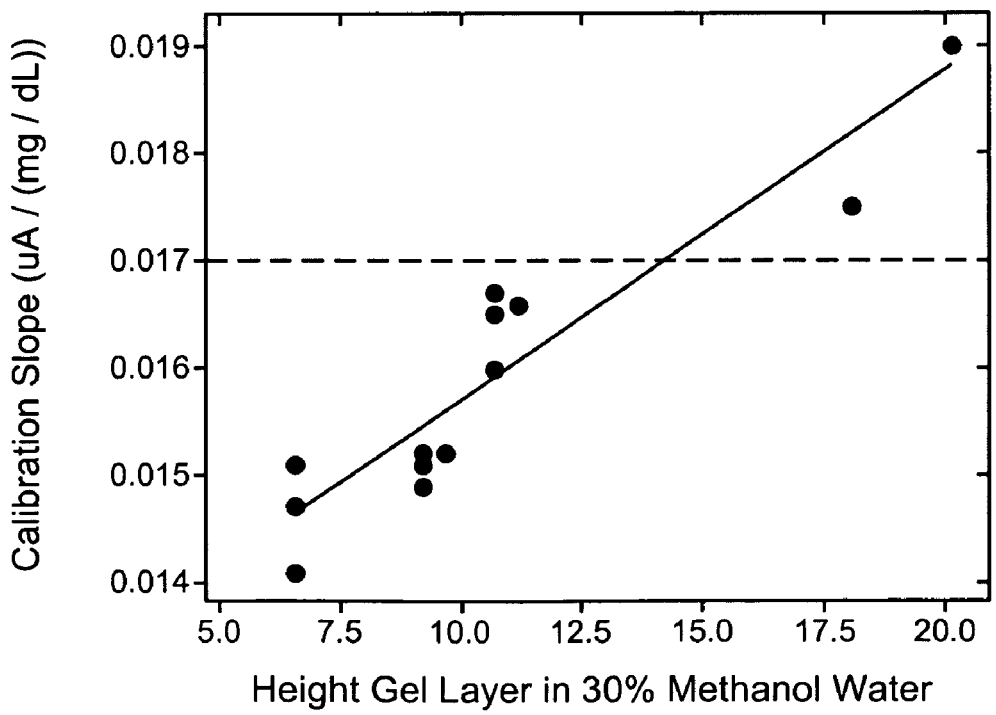
FIG. 2 is a graph depicting a relationship between wetability (measured as gel layer height (mm) in a 30% methanol and water solution) of a representative hydrophobic silica material and a calibration characteristic (i.e., calibration slope) of an electrochemical-based analytical test strip that employs an enzymatic reagent ink comprising the representative hydrophilic silica material.

FIG. 2 is a graph depicting one such first relationship between wetability of a representative hydrophobic silica material commercially available under the tradename Cab-o-Sil (Cabot Corp, Billerica, Mass., USA) and the calibration slope of electrochemical-based analytical test strips configured for the determination of glucose in blood that utilize an enzymatic reagent ink containing that representative hydrophobic silica material. In FIG. 2, wetability is measured as a gel layer height per the procedure described below. For the analytical test strip configuration employed to generate FIG. 2, an acceptable calibration slope is a calibration slope greater than about 0.017 uA/mg/dL and is indicated in FIG. 2 by the dashed horizontal line.

The first relationship derived for a representative hydrophobic silica material (such as Cab-o-Sil) has been unexpectedly found to be beneficial for methods that employ a different (i.e., non-identical) particular hydrophobic silica material in subsequent steps. For example, when the representative hydrophobic silica material is Cab-o-Sil TS610, the first relationship can be employed even when the determination of a second relationship and combining steps (described further below) use the commercially available hydrophobic silica materials H15, H18 (both available from Wacker Chemie A G, Stuttgart, Germany), or Aerosil (available from Evonik Degussa LTD, Düsseldorf, Germany). Therefore, methods according to embodiments of the present are simple and easy to use with a wide variety of hydrophobic silica materials including, for example, fumed silica materials.

FIG. 2 clearly indicates that the calibration slope is a linear function of the hydrophobic silica material's wetability (as depicted by the linear solid line). It should be noted that various manufacturing batches of the representative hydrophobic silica material were employed to generate FIG. 2. Such batch-to-batch variability in wetability of the hydrophobic silica material can result in an enzymatic reagent ink with acceptable calibration characteristics (such as a slope greater than 0.017 in FIG. 2) for certain batches or unacceptable characteristics (i.e., a slope of less than 0.017 in FIG. 2) for other batches when conventional manufacturing techniques are employed. However, methods according to embodiments of the present invention beneficially enable the successful use of a wide range of hydrophobic silica materials while accommodating batch-to-batch variability in the hydrophilic silica materials.

Once apprised of the present disclosure, one skilled in the art will recognize that suitable means of determining wetability other than gel layer height or gel layer volume can be employed in methods according to the present invention. For example, spectroscopic techniques can be employed to measure wetability. In addition, other suitable representative hydrophobic silica materials can be employed and other suitable calibration characteristics (such as calibration intercept) can be employed in embodiments of the present invention.

At step 120 of FIG. 1, process 100 includes determining a second relationship defining wetability of a mixture of a particular hydrophobic silica material and a particular surfactant across a range of relative amounts of the particular hydrophobic silica material and particular surfactant.

As noted above, the particular hydrophobic silica material can be the same as the representative hydrophobic material employed in step 110 or a different (i.e., non-identical) hydrophobic silica material. Examples of hydrophobic silica materials that can be employed in methods according to the present invention include, for example, the commercially available hydrophobic silica materials H15 and H18 (Wacker Chemie AG, Stuttgart, Germany; a synthetic, hydrophobic, amorphous silica produced via flame hydrolysis) and the commercially available hydrophobic silica material Aerosil (Evonik Degussa LTD, Düsseldorf, Germany). Cab-o-Sil, H15 and H18 are examples of fumed silica materials, also know as pyrogenic silicas.

Figure 3:
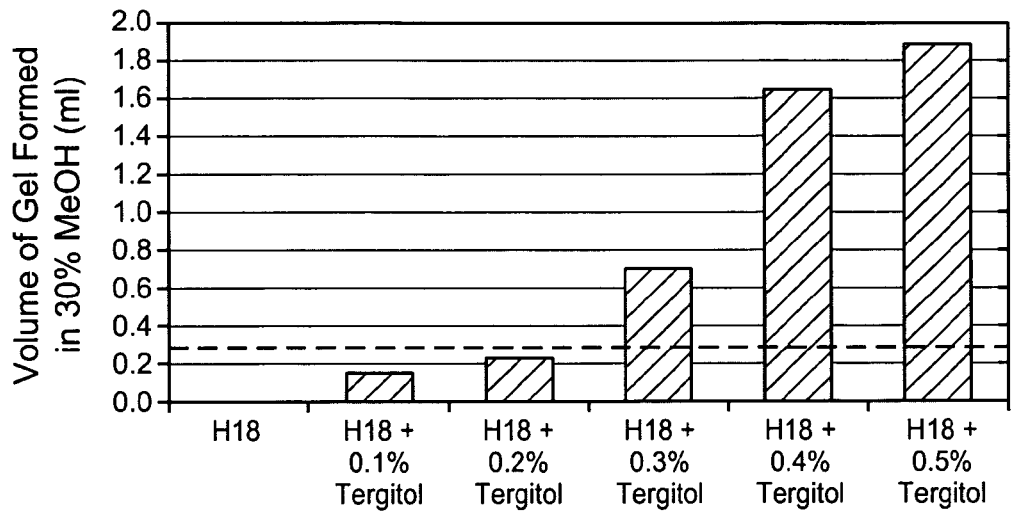
FIG. 3 is a bar graph of wetability (measured as gel volume in a 30% methanol solution) of a mixture of a particular hydrophobic silica material (i.e., H18) and a particular surfactant (i.e., Tergitol) across a range of relative amounts of H18 and Tergitol represented as a Tergitol v/v percentage.

FIG. 3 is a bar graph of wetability (measured as gel volume in a 30% methanol solution) of a mixture of a particular hydrophobic silica material (i.e., H18) and a particular surfactant (i.e., Tergitol) across a range of relative amounts of H18 and Tergitol depicted as a Tergitol v/v percentage. FIG. 3, therefore, serves to illustrate an exemplary second relationship between wetability of a mixture of a particular hydrophilic silica (i.e., H18) and a particular surfactant (Tergitol) and relative amounts of the particular hydrophilic silica material and particular surfactant in the mixture. It should be noted that in FIG. 3, the v/v notation refers to the volumetric ratio of surfactant in 8 ml of methanol-water solution with the surfactant being present at a constant weight of 0.1 g (see the wetability procedure description below).

Figure 4:
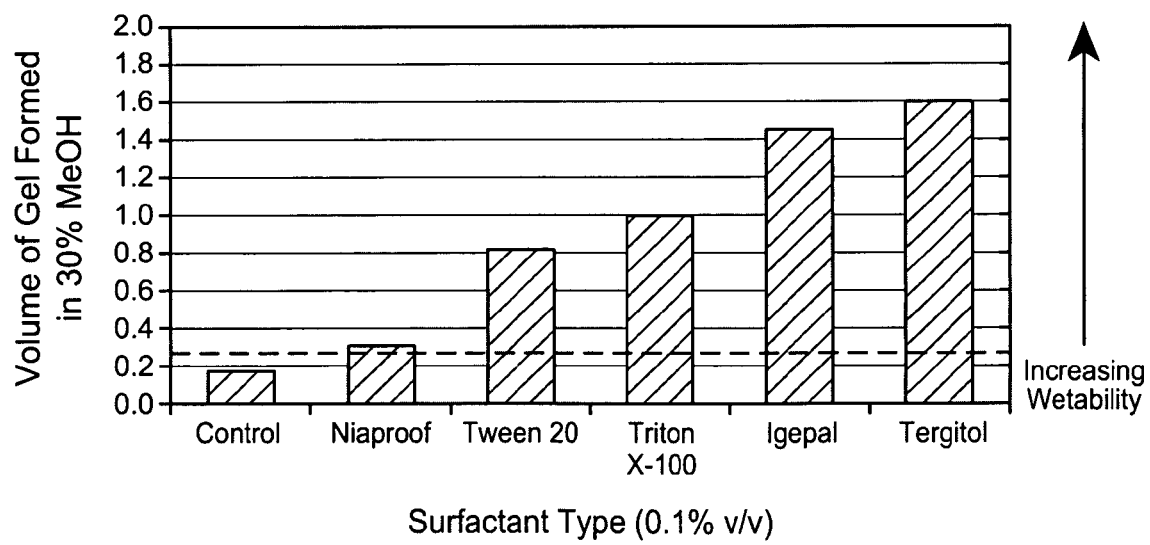
FIG. 4 is a bar graph of wetability (measured as gel volume in a 30% methanol solution) for mixtures of a particular hydrophobic silica material (i.e., Cab-o-Sil) with a variety of particular surfactants, all at relative concentrations of 0.1% v/v.

It has been determined that non-ionic surfactants are particularly suitable for use in methods according to the present invention. For example, FIG. 4 is a bar graph of wetability (measured as gel volume in a 30% methanol solution) for mixtures of a particular hydrophobic silica material (i.e., Cab-o-Sil) with a variety of surfactants, all at relative concentrations of 0.1% v/v. The horizontal dashed line of FIG. 4 indicates the minimum wetability required to provide an acceptable calibration characteristic (such as calibration slope and/or calibration intercept). In FIG. 4, the v/v notation again refers to the volumetric ratio of surfactant in 8 ml of methanol-water solution with the surfactant being present at a constant weight of 0.1 g (see the wetability procedure description below).

The control group of FIG. 4 had no added surfactant and a wetability that is insufficient to provide an acceptable calibration characteristic. FIG. 4 illustrates that the addition of various surfactants causes an increase in the wetability of the hydrophobic silica material to varying extents. Tergitol and Igepal when added to a final concentration of 0.1% v/v result in the largest increase in wetability. Niaproof (an ionic surfactant) results in only a marginal increase in wetability.

Both Igepal and Tergitol are polyglycol ether aromatic ring containing (non-ionic) surfactants. Such non-ionic surfactants appear to be the most suitable reagents for achieving maximum wetability. Triton X 100 is a polyethylene glycol tert-octylphenyl ether (non-ionic) surfactant. This class of surfactants does not improve wetability to the same extent as Igepal and Tergitol but can be suitable for use in methods according to the present invention. Niaproof, sodium 7-ethyl-2-methyl-4-undecyl sulfate, is an anionic surfactant and resulted in the least wetability increase when employed at 0.1% v/v.

When comparing FIGS. 3 and 4, it should be noted that H18 is an extremely hydrophobic silica material and, therefore, greater relative amounts of surfactant are needed to increase the wetability to the degree necessary to achieve an acceptable calibration characteristic in comparison to Cab-o-Sil. However, even an extremely hydrophobic silica material such as H18 can be rendered suitable for use in enzymatic reagent inks by methods according to embodiments of the present invention.

Referring again to FIG. 1, at step 130 of process 100 an amount of the particular hydrophobic silica material, an amount of the particular surfactant, and an amount of enzyme are combined to form an enzymatic reagent ink. Moreover, the amounts of the particular hydrophobic silica material and the particular surfactant are predetermined based on the second relationship to provide at least the minimum wetability defined by the first relationship and, therefore, an acceptable and predetermined calibration characteristic. For example, the amount of surfactant can be predetermined such that its concentration is appropriate to provide the desired wetability of the amount of hydrophobic silica material during the combination step while manufacturing of an enzymatic reagent ink and, thereby, an acceptable and predetermined calibration characteristic.

Figure 5:
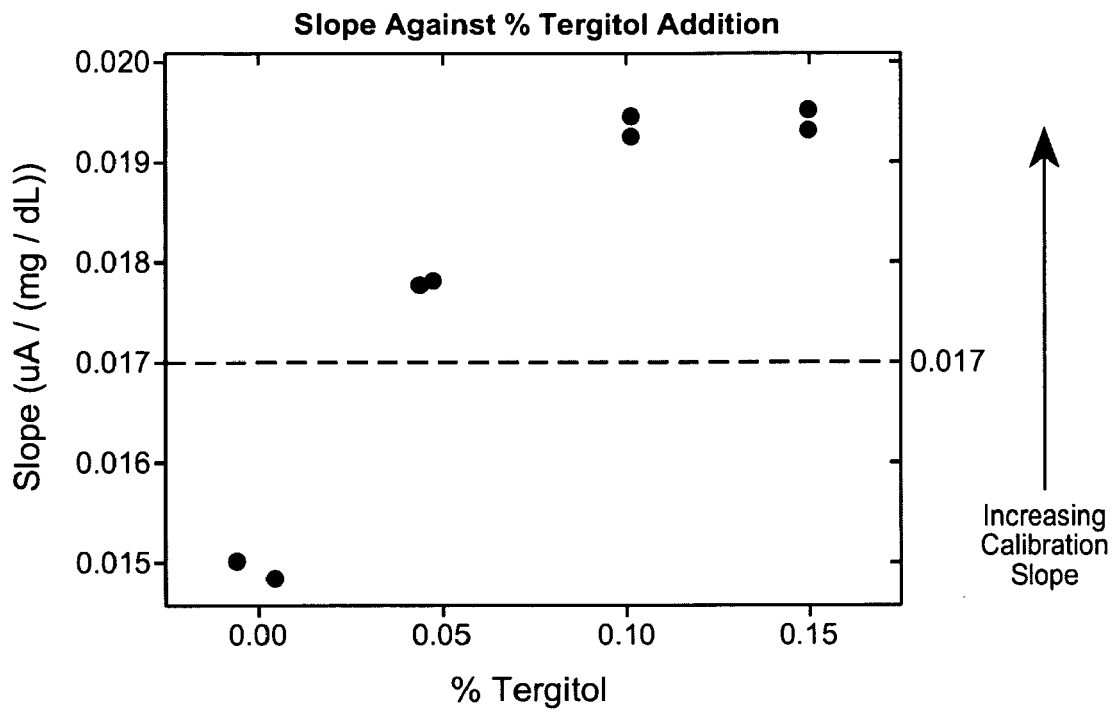
FIG. 5 is a plot of calibration slope versus surfactant percentage (v/v) for an enzymatic reagent ink comprising Cab-o-Sil hydrophobic silica material and Tergitol surfactant.
Figure 7:
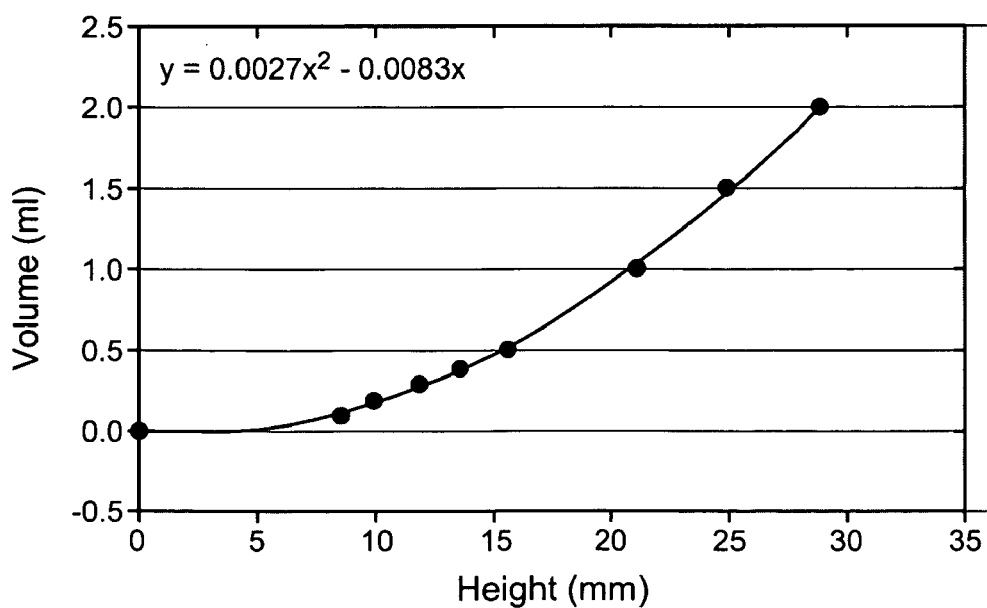
FIG. 7 is a graph depicting a relationship between gel volume and gel height as can be employed in using gel height and volume as a measure of wetability in methods according to the present invention.

Methods according to the present invention are beneficial in that they enable the ready use of hydrophobic silica materials in enzymatic reagent inks even though the hydrophobic nature of the hydrophobic materials would normally preclude their use. In other words, silica materials that are too hydrophobic for ready use are made suitable for use by incorporating an amount of surfactant that is determined by the first and second relationships described herein. For example, FIG. 4 indicates that the control batch of Cab-o-Sil hydrophobic silica material is too hydrophobic for successful use in an enzymatic reagent ink. However, incorporation of Tergitol at an approximate 0.1% (v/v) amount (i.e., at a volumetric concentration of 0.1% during the combining step) renders the hydrophobic silica material suitable for use without costly or time consuming manufacturing processes. This conclusion is supported by the data of FIG. 5 which illustrate that the addition of Tergitol to Cab-o-Sil enables a suitable calibration slope (i.e., a calibration slope greater than 0.017) whereas the absence of surfactant resulted in an unacceptable calibration slope (i.e., a calibration slope of less than 0.017). In this regard, it should be noted that in FIG. 5, the v/v % Tergitol is a volumetric percent based on the addition of Tergitol to a buffer solution prior to combination with Cab-o-Sil (see the Preparation of Enzymatic Reagent Ink section below)

It is hypothesized without being bound, that the combination of a hydrophobic silica material and a surfactant in amounts per embodiments of the present invention produces a reagent layer on analytical test strips with a suitably open structure (porosity) and/or density that results in acceptable calibration characteristics. Although such density and porosity can be controlled to some extent by increasing various mixing times during enzymatic ink preparation, such increases can lead to degradative heating and extended preparations times and costs.

Furthermore, experimental results indicate that the inclusion of surfactant according to embodiments of the present invention does not adversely affect analytical test strip functionality. For example, no adverse effects with respect to potential interfering compounds (such as L-Dopamine, Uric acid, Ascorbic acid, paracetamol (acetaminophen) and gentisic acid were found and analytical test strip stability was identical to analytical test strips containing no surfactant.

The first and second relationships described herein can be determined using simple laboratory equipment. Methods according to the present invention are, therefore, beneficially inexpensive. Moreover, since the methods employ simple hydrophobic silica materials (such as fumed silica materials), they obviate any need to employ sophisticated silica materials with both hydrophilic and hydrophobic properties.

An enzymatic reagent ink according embodiments of the present invention includes an amount of hydrophobic silica material (e.g., an amount of a fumed silica material), an amount of surfactant (such as a non-ionic surfactant); and an amount of enzyme (for example, glucose oxidase). The amounts of the hydrophobic silica material and the surfactant present in the enzymatic reagent ink is predetermined based on first and second relationships. The first relationship is a relationship between wetability of a representative hydrophobic silica material and a first calibration characteristic of an analytical test strip that includes an enzymatic reagent ink containing the representative hydrophobic silica material. In addition, such a first relationship defines a minimum wetability that provides an acceptable first calibration characteristic. The second relationship is a relationship defines wetability of a mixture of the hydrophobic silica material and the surfactant across a range of relative amounts of the hydrophobic silica material and the surfactant. The relative amounts of the hydrophobic silica material and the surfactant in the enzymatic reagent ink are predetermined to provide at least the minimum wetability defined by the first relationship, and therefore, an acceptable first calibration characteristic.

Once apprised of the present disclosure, one skilled in the art will recognize that enzymatic reagent inks according to the present invention are those inks that are manufactured according to the methods of the present invention. Therefore, components, characteristics and benefits described herein with respect to the methods of the present invention also apply to enzymatic reagent inks of the present invention.

An example of an enzymatic reagent ink according to the present invention has the following formulation:

| | |
|---|---|
| DC 1500 Anti-foam | 20.3% by mass |
| Polyvinyl alcohol | 0.7% by mass |
| Citric acid | 0.6% by mass |
| Trisodium citrate | 2.0% by mass |
| Tergitol surfactant | 0.07% by mass |
| Polyvinylpyrrolidone-vinyl acetate copolymer | 0.7% by mass |
| Hydroxyl-ethyl cellulose | 3.5% by mass |
| Cab-o-Sil hydrophobic silica | 5.0% by mass |
| Potassium ferricyanide | 20% by mass |
| Glucose Oxidase | 1.9% by mass |
| Water | 65% by mass |

A suitable method of preparing the enzymatic reagent ink described immediately above is detailed below. Once apprised of this disclosure, including the enzymatic reagent ink preparation description below, one skilled in the art will recognize that the specific amount of particular surfactant employed in methods according to the present invention is dependent not only on the first and second relationships described herein but also on details of the manufacturing process that are readily understandable to one skilled in the art. For example, in the enzymatic reagent ink preparation description below, a specific amount of 10 ml of Tergitol is added to a buffer volume of approx. 10,000 ml to achieve a desired 0.1% v/v amount, with the 0.1 v/v % having been determined based on first and second relationships of a method according to an embodiment of the present invention. The surfactant is then present at the desired v/v % (such as a v/v % greater than 0.10 v/v %) when combined with the hydrophobic silica material.

In general, analytical test strips according to the present invention include a substrate and a reagent layer disposed on a portion of the substrate. The reagent layer includes an enzymatic reagent ink comprising an amount of hydrophobic silica material, an amount of surfactant; and an amount of enzyme. The relative amounts of the hydrophobic silica material and the surfactant in the enzymatic reagent ink is predetermined using a first relationship and a second relationship. The first relationship is between wetability of a representative hydrophobic silica material and at least a first calibration characteristic (such as calibration slope and/or calibration intercept) of an analytical test strip that includes an enzymatic reagent ink containing the representative hydrophobic silica material. In addition, the first relationship defines a minimum wetability that provides an acceptable first calibration characteristic.

The second relationship defines wetability of a mixture of the hydrophobic silica material and the surfactant across a range of relative amounts of the hydrophobic silica material and the surfactant. The predetermined relative amounts of the hydrophobic silica material and the surfactant employed in the enzymatic reagent ink provide at least the minimum wetability defined by the first relationship and, therefore, an acceptable first calibration characteristic.

FIG. 6 is a simplified exploded perspective view of an electrochemical-based analytical test strip 200 according to the present invention that is configured to determine glucose in a blood sample.

Electrochemical-based analytical test strip 200 includes an electrically-insulating substrate 212 (also referred to simply as a substrate), a patterned conductor layer 214 (defining three electrodes), an insulation layer 216 (with electrode exposure window 217 extending therethrough), a reagent layer 218, a patterned adhesive layer 220, a hydrophilic layer 222 and a top film 224.

Electrically-insulating substrate 212 can be any suitable electrically-insulating substrate known to one skilled in the art including, for example, a nylon substrate, polycarbonate substrate, a polyimide substrate, a polyvinyl chloride substrate, a polyethylene substrate, a polypropylene substrate, a glycolated polyester (PETG) substrate, or a polyester substrate. The electrically-insulating substrate can have any suitable dimensions including, for example, a width dimension of about 5 mm, a length dimension of about 27 mm and a thickness dimension of about 0.5 mm.

Insulation layer 216 can be formed, for example, from a screen printable insulating ink. Such a screen printable insulating ink is commercially available from Ercon of Wareham, Mass. U.S.A. under the name "Insulayer." Patterned adhesive layer 220 can be formed, for example, from a screen-printable pressure sensitive adhesive commercially available from Apollo Adhesives, Tamworth, Staffordshire, UK.

Hydrophilic layer 222 can be, for example, a clear film with hydrophilic properties that promote wetting and filling of electrochemical-based analytical test strip 200 by a fluid sample (e.g., a whole blood sample). Such clear films are commercially available from, for example, 3M of Minneapolis, Minn. U.S.A. Top film 224 can be, for example, a clear film overprinted by black decorative ink. A suitable clear film is commercially available from Tape Specialities, Tring, Hertfordshire, UK.

Reagent layer 218 can include any suitable enzymatic reagents, with the selection of enzymatic reagents being dependent on the analyte to be determined. For example, if glucose is to be determined in a blood sample, reagent layer 218 can include oxidase or glucose dehydrogenase along with other components necessary for functional operation. However, according to embodiments of the present invention reagent layer 218 includes, at least, an enzymatic reagent ink according to an embodiment of the present invention.

Electrochemical-based analytical test strip 200 can be manufactured, for example, by the sequential aligned formation of patterned conductor layer 214, insulation layer 216 (with electrode exposure window 217 extending therethrough), reagent layer 218, patterned adhesive layer 220, hydrophilic layer 222 and top film 224 onto electrically-insulating substrate 212. Any suitable techniques known to one skilled in the art can be used to accomplish such sequential aligned formation, including, for example, screen printing, photolithography, photogravure, chemical vapour deposition and tape lamination techniques.

Procedure for Measuring Wetability as Gel Height or Gel Volume

Materials and Reagents: analytical balance, glass weighing boats, Scientific Industries Vortex Genie 2, Hettich Universal 16 swing-out centrifuge, Mitutoyo Absolute Digimatic calipers, TPP 91015-graduated plastic centrifuge tubes, AnalaR water, Methanol (spectrophotometric grade), hydrophobic silica material and surfactant as appropriate.

Methodology: Weigh out 0.1 g of hydrophobic silica material and, if appropriate a desired amount of surfactant using the analytical balance and glass weighing boats. Transfer the hydrophobic silica material, and surfactant if desired, to a plastic centrifuge tube. Add 8 ml of 30% (v/v) methanol/water solution. Disperse the hydrophobic silica material and, if present the surfactant, by shaking the centrifuge tube and then vortex the resulting mixture for 3 minutes using the maximum setting of the Scientific Industries Vortex Genie 2. Next, place the centrifuge tube into the Hettich Universal 16 swing-out centrifuge ensuring that the centrifuge buckets are balanced. Centrifuge for 5 minutes at 4,500 rpm.

Remove the centrifuge tubes and, with the Mitutoyo Absolute Digimatic calipers, measure the height of the gel layer (which is at the bottom of tube) and the height of the un-wetted fumed silica (top of the tube). If desired, the chart or equation of FIG. 6 can be employed to convert gel height (in mm) to gel volume (in ml).

Preparation of Enzymatic Reagent Ink Using Hydrophobic Silica Material

The following procedure was employed to prepare the exemplary enzymatic reagent ink described herein.

A PVA-Antifoam-citric acid solution was prepared by combining 0.5 ml of DC 1500 Antifoam (commercially available from BDH/Merek Ltd.) with 7500 grams of water (AnalaR, available from BDH/Merck Ltd.). Next, 90 grams of polyvinyl alcohol ("PVA," Sigma-Aldrich, MW 85,000-124,000, 87%-89% hydrolysed) was added to the solution and homogenized at >7000 RPM for 2 hours. After homogenization, 81.5 grams of citric acid was mixed into the solution.

A pH adjusting solution was prepared by mixing 270 grams of trisodium citrate into 1000 ml of water. The pH of the PVA-Antifoam-citric acid solution was then adjusted to pH 5 by adding a sufficient amount of the trisodium citrate solution.

The pH 5 solution was filtered through a 125 micron sieve and transferred to a 30 liter stainless steel pot. Additional water was added to the 30 liter steel pot until the total solution weight was 9250 grams. 44.5 mL of DC 1500 Antifoam was then added to the stainless steel pot. 10 mL of Tergitol was added to the stainless steel pot.

A 90 mm diameter mixer blade was attached to a Dispersmat mixer and mounted to the stainless steel pot such that the mixer blade was 2 centimeters above the bottom of the pot. The mixer was set at 800 RPM and then 90 grams of polyvinylpyrrolidone-vinyl acetate (PVP/VA S-630 co-polymer, commercially available from the ISP Company, and which has a 60/40 ratio and a molecular weight of 24,000 to 30,000) and 449 grams of hydroxyl-ethyl cellulose ("HEC," commercially available as Natrosol 250G) were added during first two minutes of mixing. Next, the mixing speed was increased to 5500 RPMs and continued for five additional minutes, resulting in a HEC solution.

After the mixing period, the HEC solution was transferred to a 15 liter keg and mixed gently (i.e., roll) for 12 to 25 hours. The viscosity was then measured and confirmed to be within the range of 13,000 to 17,000 cP (measured at 25° C. and 5 RPMs).

The rolled HEC solution was equilibrated to between 7° C. and 10° C. Next, 9000 grams of the rolled and equilibrated HEC solution was mixed with 675 grams of hydrophobic silica material (Cab-o-Sil, commercially available from Cabot Corp., Billerica, Mass., 01821-7001, USA) in a 30 liter stainless steel pot to form an HEC/silica mixture.

A 175 mm diameter mixer blade was attached to the Dispersmat mixer and mounted to the stainless steel pot so that the mixer blade was at the bottom of the pot. The combined HEC/silica mixture was mixed at 2600 RPM for 16 minutes. The density of the formulation was then measured (using a Cole-Parmer Pycnometer) to determined to be in the range of from about 0.85 g/cm$^3$ to about 1.015 g/cm$^3$.

The HEC/silica mixture was then transferred to a 15 liter keg and rolled gently for 8 to 16 hours. The viscosity was then measured and confirmed to be within 37,000 to 50,000 cP (measured at 25° C. and 10 RPMs).

4515 grams of HEC/silica mixture was combined with 1386 grams of potassium ferricyanide and 126 grams of glucose oxidase in a 15 liter stainless steel pot. A 125 mm diameter mixer blade was attached to the Dispersmat mixer and mounted to the stainless steel pot so that the mixer blade was at the bottom of the pot and the mixture mixed at 1500 RPMs for 15 minutes. After mixing, the pH was in the range from about 4.8 to 5.4 and the viscosity was in the range from about 36,000 to 48,000 cP (measured at 25° C. and 10 RPM). Thereafter, the enzymatic reagent ink was ready for screen printing onto electrodes and/or substrates during the manufacturing of electrochemical-based analytical test strips configured for the determination of glucose in a blood sample.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that devices and methods, compositions and devices within the scope of these claims and their equivalents be covered thereby.

What is claimed is:

1. A method for manufacturing an enzymatic reagent ink for use in analytical test strips, the method comprising:
    determining a first relationship between wetability of a representative hydrophobic silica material and at least a first calibration characteristic of an analytical test strip that includes an enzymatic reagent ink containing the representative hydrophobic silica material, the first relationship defining a minimum wetability that provides a first calibration characteristic of a calibration slope and/or a calibration intercept;
    determining a second relationship defining wetability of a mixture of a particular hydrophobic silica material and a particular surfactant across a range of relative amounts of the particular hydrophobic silica material and the particular surfactant; and
    combining, at least, relative amounts of the particular hydrophobic silica material and the particular surfactant, and an amount of enzyme to form an enzymatic reagent ink that is devoid of the representative hydrophobic silica material;
    wherein the relative amounts of the particular hydrophobic silica material and the particular surfactant in the combining step are predetermined based on the second relationship to provide at least the minimum wetability defined by the first relationship and, therefore, the first calibration characteristic of a calibration slope and/or a calibration intercept; and
    wherein the representative hydrophobic silica material and the particular hydrophobic silica materials are non-identical hydrophobic silica materials.

2. The method of claim 1 wherein the representative hydrophobic silica material and the particular hydrophobic silica material are hydrophobic fumed silica materials.

3. The method of claim 1 wherein the particular surfactant is a non-ionic surfactant.

4. The method of claim 3 wherein the non-ionic surfactant is a polyglycol ether aromatic ring containing non-ionic surfactant.

5. The method of claim 1 wherein the at least a first calibration characteristic is a calibration slope.

6. The method of claim 1 wherein the at least a first calibration characteristic is a calibration intercept.

7. The method of claim 1 wherein the wetability is determined as gel height in a methanol and water solution.

8. The method of claim 1 wherein wetability is determined as gel volume in a methanol and water solution.

9. The method of claim 1 wherein the enzymatic reagent ink is a screen printable enzymatic reagent ink.

10. The method of claim 1 wherein the analytical test strip is an electrochemical-based analytical test strip configured for the determination of glucose in a blood sample.

11. The method of claim 1 wherein the enzyme is glucose oxidase.

12. The method of claim 1 wherein the amount of the particular surfactant is such that the particular surfactant is present at a concentration of at least 0.10% v/v when being combined with the amount of particular hydrophobic silica material.

* * * * *